United States Patent [19]

Ueno

[11] Patent Number: 5,061,178
[45] Date of Patent: Oct. 29, 1991

[54] WAX SHAPING TOOL

[75] Inventor: Masato Ueno, Hiroshima, Japan

[73] Assignee: Molten Corporation, Hiroshima, Japan

[21] Appl. No.: 613,743

[22] PCT Filed: Apr. 6, 1989

[86] PCT No.: PCT/JP89/00373
§ 371 Date: Dec. 5, 1990
§ 102(e) Date: Dec. 5, 1990

[87] PCT Pub. No.: WO90/11733
PCT Pub. Date: Oct. 18, 1990

[51] Int. Cl.$^5$ .................. A61C 3/00; A61C 19/00; B67D 5/62
[52] U.S. Cl. .................. 433/32; 222/146.5
[58] Field of Search .................. 433/32; 222/390, 392, 222/146.1, 146.5; 219/385, 469; 401/2, 13, 55, 75

[56] References Cited

U.S. PATENT DOCUMENTS

| | | | |
|---|---|---|---|
| 1,449,517 | 3/1922 | Lane | 401/55 |
| 1,905,987 | 4/1933 | Lane | 219/21 |
| 2,097,098 | 10/1937 | Hiscox | 219/21 |
| 2,119,908 | 6/1938 | Ellis | 219/21 |
| 2,243,400 | 5/1941 | Stack | 219/21 |
| 2,468,818 | 5/1949 | Fox | 219/21 |
| 3,774,809 | 11/1973 | Bratton | 222/137 |
| 3,800,122 | 3/1974 | Farmer | 219/239 |
| 3,902,043 | 8/1975 | Rogan | 219/242 |
| 4,301,357 | 11/1981 | Huffman | 219/229 |
| 4,770,633 | 9/1988 | Ueno | 433/32 |
| 4,813,870 | 3/1989 | Pitzen et al. | 433/90 |

Primary Examiner—John J. Wilson
Assistant Examiner—Cindy A. Cherichetti
Attorney, Agent, or Firm—Armstrong, Nikaido, Marmelstein, Kubovcik & Murray

[57] ABSTRACT

A wax shaping tool of the present invention is a tool which is used in manufacturing an artificial denture model by a dental technician. The tool comprises a tubular handle portion 10 having a slit 12 extending in an axial direction for interconnecting an internal bore with the external space, a wax cartridge holder 13 provided on upper side of the handle portion including edges of the slit for slidably provided guiding a wax cartridge 16, a roller 14 rotatably onto said handle portion so as to protrude from a peripheral part thereof, a first drive which removably holds a rear end of the wax cartridge and is movable in an axial direction in the wax cartridge holder, a second drive (20, 21, 23, 24; 33, 34, 35, 36) provided in said handle portion for converting a rotating movement of the roller into the rectilinear movement and for transmitting the motion to the first drive, a spatula 26 provided on a front end of the handle portion, a wax melter portion 27 for contacting and melting the wax cartridge portion projected out of a front end the wax cartridge holder, and a heater 28 for heating up said spatula and said wax melter portion. Since the amount of melted wax can be freely controlled according to the rotation of the roller by fingers, said tool can be easily used.

4 Claims, 4 Drawing Sheets

WAX SHAPING TOOL

TECHNICAL FIELD

The present invention relates to a wax shaping tool used in forming an artificial denture model with dental wax on a dental cast obtained from a patient.

BACKGROUND ART

In building and shaping wax in the field of denture work, the following steps are usually repeated more than ten times for one tooth; (a) first to heat up a spatula and to soften or melt solid wax and to scoop it by means of the heated spatula; (b) then to heat it up again to make it in a liquid form; and (c) to build it up at a region where wax shaping is to be performed.

In this conventional procedure, the point of regard of a dental technician moves outside of the region whenever the above steps are repeated. Accordingly, it is difficult for the dental technician to concentrate his attention on a wax shaping work, and consequently an efficiency of the work is extremely low.

In order to improve the efficiency of this troublesome work, there has been proposed a construction combining a heater and a spatula and providing direct heating of the spatula by the heater. Examples of such construction can be seen in U.S. Pat. No. 1,905,987, U.S. Pat. No. 2,097,098, U.S. Pat. No. 2,119,908, U.S. Pat. No. 2,468,818, U.S. Pat. No. 3,800,122, U.S. Pat. No. 3,902,043 and U.S. Pat. No. 4,301,357.

However, even if the spatula having the proposed construction is employed, the work includes essentially a step for dipping wax from another place and still requires the dental technician to make his point of regard move outside of the region where wax shaping is to be performed. Accordingly, the improvement in the efficiency of the work is not yet satisfactory.

Moreover, in another example, a construction of the conventional tool is disclosed in U.S. Pat. No. 2,243,400 wherein a heater and a wax reservoir are provided in a handle portion and wax melted by the heater is delivered to a spatula formed at a tip portion. However, since the molten wax is prestored in wax reservoir, as to the above example the construction has a drawback that there might occur a degradation of wax or a separation of wax component before the molten wax is delivered to the spatula and as a result the wax might become inadequate for the denture work in which a high tolerance is required.

The present inventors have proposed a tool disclosed in U.S. Pat. No. 4,770,633 in order to eliminate the drawback. The above-mentioned tool is generally constructed to slip down a wax cartridge by the self gravity. However, the subsequent study has proved that the construction is not necessarily satisfactory with respect to the operation.

For example, there is a problem that the wax cartridge falls out of the tool when the rear end of the tool is tilted downward in the course of slipping by self gravity of the wax cartridge for any reason.

An object of the present invention is to provide a wax shaping tool which can completely control a forward and backward movement of the wax cartridge, and therefore, which can freely adjust the amount and speed of wax melting speed thereof and can operate more properly than the conventional one.

Another object of the present invention is to provide a wax shaping tool which allow a dental technician to continuously perform a wax shaping work many times without making his point of regard move outside of the region to be shaped, and therefore, which enables a wax building and shaping work to be carried out rapidly and efficiently.

A further object of the present invention is to provide a wax shaping tool wherein solid wax is melted just before a wax building work so that the work can be carried out with avoiding the degradation of wax or the separation of wax component.

A further object of the present invention is to provide a wax shaping tool wherein a solid wax cartridge, which is apt to be softened and deformed by an external force, can be fed without deformation, bending or the like.

DISCLOSURE OF THE INVENTION

In accordance with the present invention, the wax shaping tool comprises a tubular handle portion having a slit extending in an axial direction for interconnecting an internal bore with external space, a wax cartridge holder provided on upper side of the handle portion including edges of said slit for slidably guiding a wax cartridge, a roller rotatably provided onto said handle portion so as to protrude from a peripheral part thereof, a first drive (a wax carrier) which removably holds a rear end of the wax cartridge and is movable in the axial direction in the wax cartridge housing portion, a second drive (a feed means) provided in said handle portion for converting the rotating movement of the roller into the rectilinear movement and transmitting it, to said first drive, a spatula provided on a front end portion of said handle portion, a wax melter portion for contacting and melting a portion of wax cartridge projected out of a front end of said wax cartridge holder and a heating portion for heating up said spatula and the wax melter portion.

BEST MODE FOR CARRYING OUT THE INVENTION

First, there is explained the first embodiment of the wax shaping tool of the present invention referring to FIGS. 1 to 5.

Figure 1:
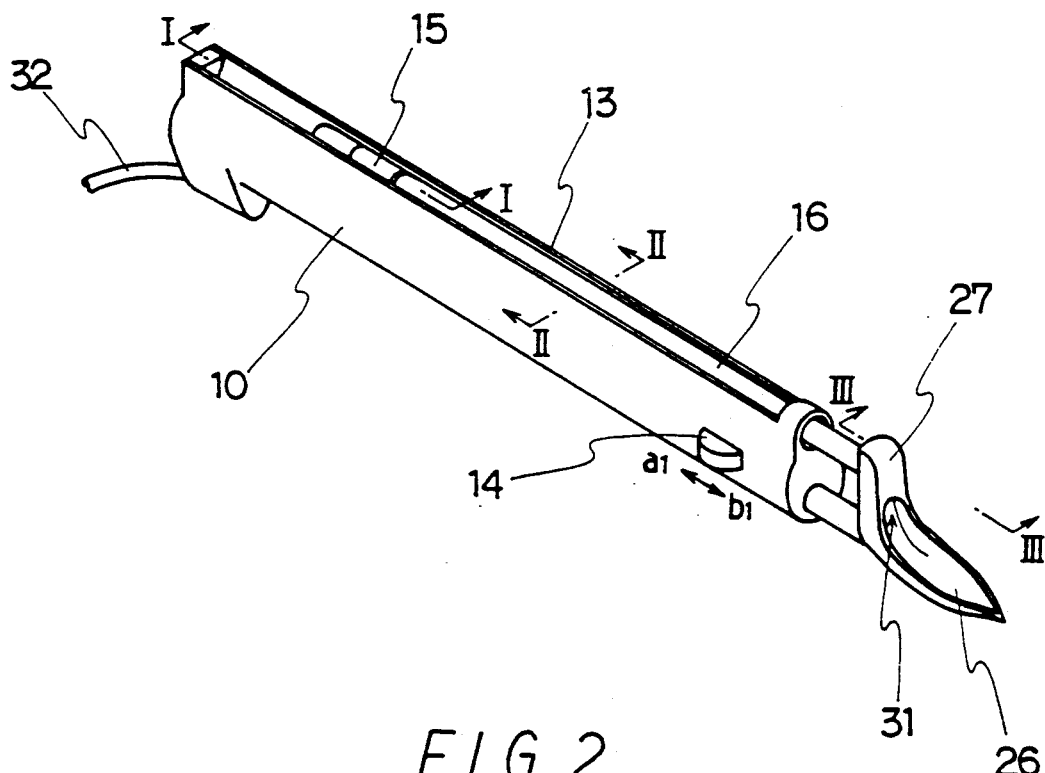
FIG. 1 is a perspective view showing the first embodiment of a wax shaping tool of the present invention.

In FIG. 1, the numeral 10 shows a handle portion which has a shape like an elongated cylinder, is formed with plastic or metallic material and has a bore 11 extending in the axial direction therein. A slit 12 is formed on the top surface of the handle portion 10, which interconnects the bore 11 with the external portion. A wax cartridge holder 13 for housing a solid wax like a rod 16 (hereinafter referred to as a wax cartridge), is provided on the top surface of the handle portion 10. The wax cartridge holder 13 comprises peripheral edge portions of the slit 12 and ribs formed on the sides thereof.

Figure 4:
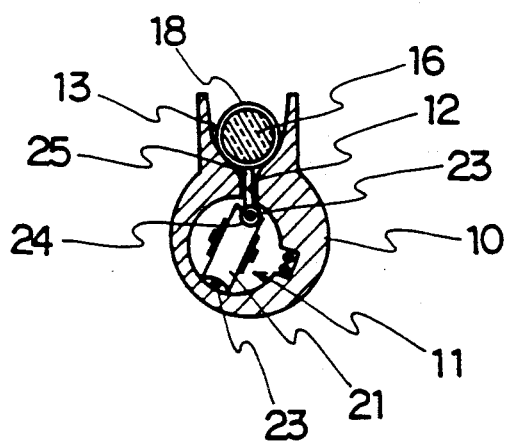
FIG. 4 is a sectional view taken along the line II—II in FIG. 1.

As shown in FIG. 4, the wax cartridge holder 13, in which a solid and cylinder-shaped wax cartridge 16 is mounted and accommodated slidably in the axial direction, is formed into a "V"-shaped groove in section, such that wax cartridge 16 having various diameters can be accommodated and guided.

Figure 2:
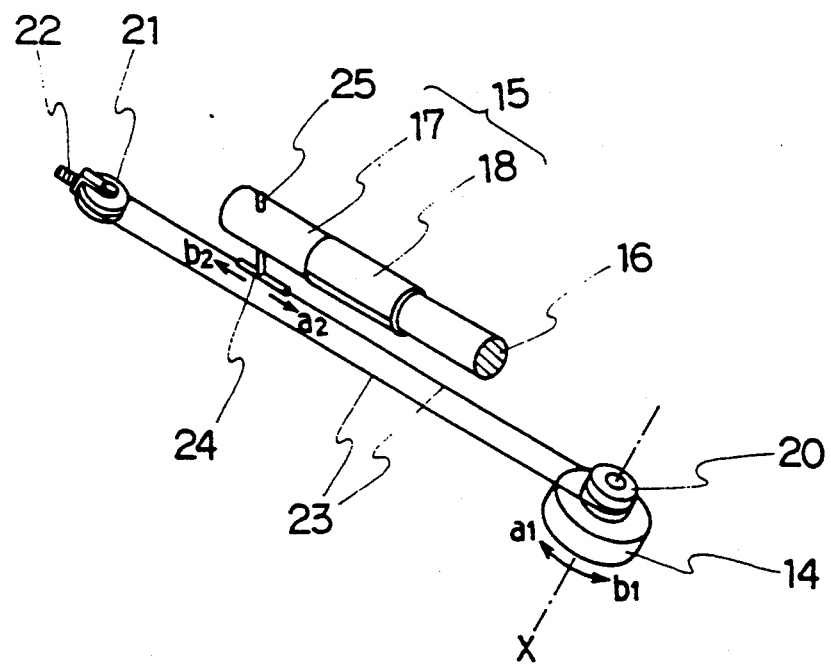
FIG. 2 is a perspective view of a wax feed mechanism in the tool in FIG. 1.

In FIGS. 1 and 2, the numeral 14 shows a roller for operation which is rotatably supported on the proximity of the front end of the handle portion 10 so that a part of the roller protrudes from the surface thereof.

Figure 3:
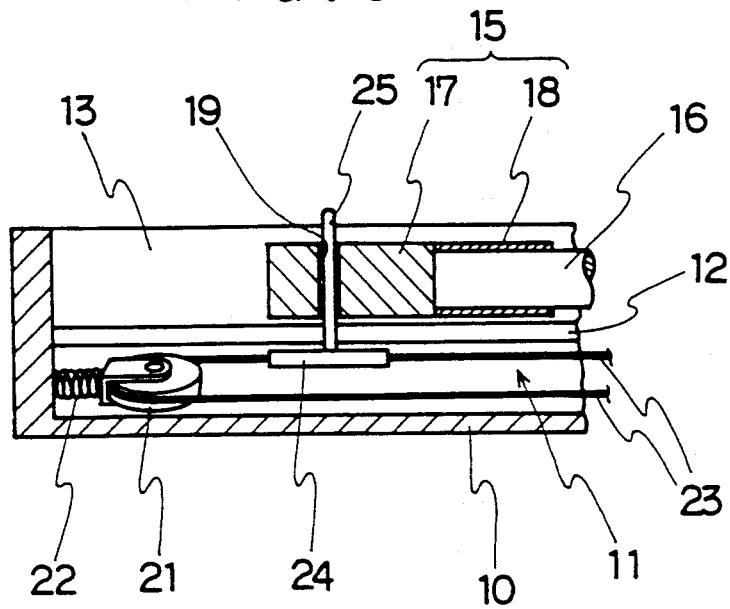
FIG. 3 is a sectional view taken along the line I—I in FIG. 1.

Furthermore, the numeral 15 in FIG. 3 is a first drive which is equipped on the rear end of the wax cartridge 16 accommodated in the wax cartridge holder 13. The first drive 15 comprises a base 17 and a clip 18 formed in the forward side thereof, and the clip 18 has a divided cylindrical body made of a elastic vinyl resin or the like. One of the divided clip 18 is opened upwardly, the rear end of the wax cartridge 16 is mounted on the other, and thereby the wax cartridge 16 is clamped taking advantage of the resilience of the clip 18. The base 17 has a through hole 19 extending in the direction of the diameter.

The wax cartridge 16 is moved backward and forward according to the back-forth movement of the above-mentioned first drive 15.

In FIG. 2, the numeral 20 shows a first pulley which is fixed on the center axis X of the above-mentioned roller 14 and positioned near the front end of the bore 11. The first pulley 20 rotates together with the roller 14. A second pulley 21 which is fixed through a spring member 22 is accommodated in the rear side of the bore 11. A string or wire 23 is strained between the first pulley 20 and the second pulley 21.

A root portion of a connector 24, which moves backward and forward corresponding to the rotating movement of the above-mentioned roller 14, is attached to the string 23. The connector 24 has a stem 25 extending in a direction transverse to the string 23, and the stem 25 penetrates the hole 19 in the base 17 in the first drive 15 through the above-mentioned slit 21. Therefore, the first drive 15 moves backward and forward according to the back-forth movement of the connector 24, and then, the wax cartridge 16 also moves in the same direction. The connector 24 can be formed with metallic material.

The first pulley 20, the second pulley 21, the string 23 and connector 24 described above are assembled to provide a wax feeding mechanism. Moreover, the first pulley 20, the second pulley 21 and the string 23 are assembled up to a conversion mechanism for converting the rotating movement into the linear movement.

A spatula 26 which has a shape almost like a dish is provided in the forward side of the handle portion 24. One end of a wax melter 27 is fixed at the rear end of the spatula 26, and the other end of the wax melter 27 projects along the line where the cartridge 16 moves on the spatula 26.

The wax melter 27 and the spatula 26 are integratedly formed with metallic material having high thermal conductivity, e.g. aluminum, copper, brass, Ni-Cr alloy, Co-Cr alloy or the like.

Figure 5:
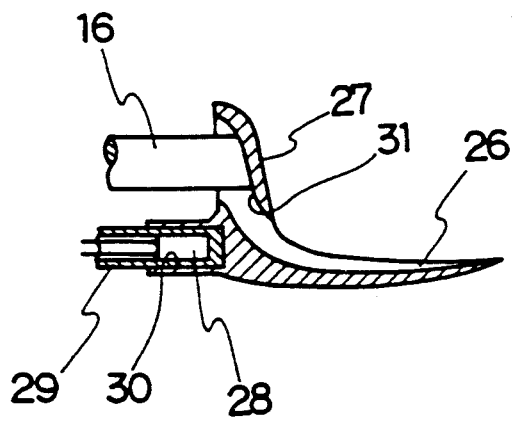
FIG. 5 is a sectional view taken along the line III—III in FIG. 1.
Figure 6:
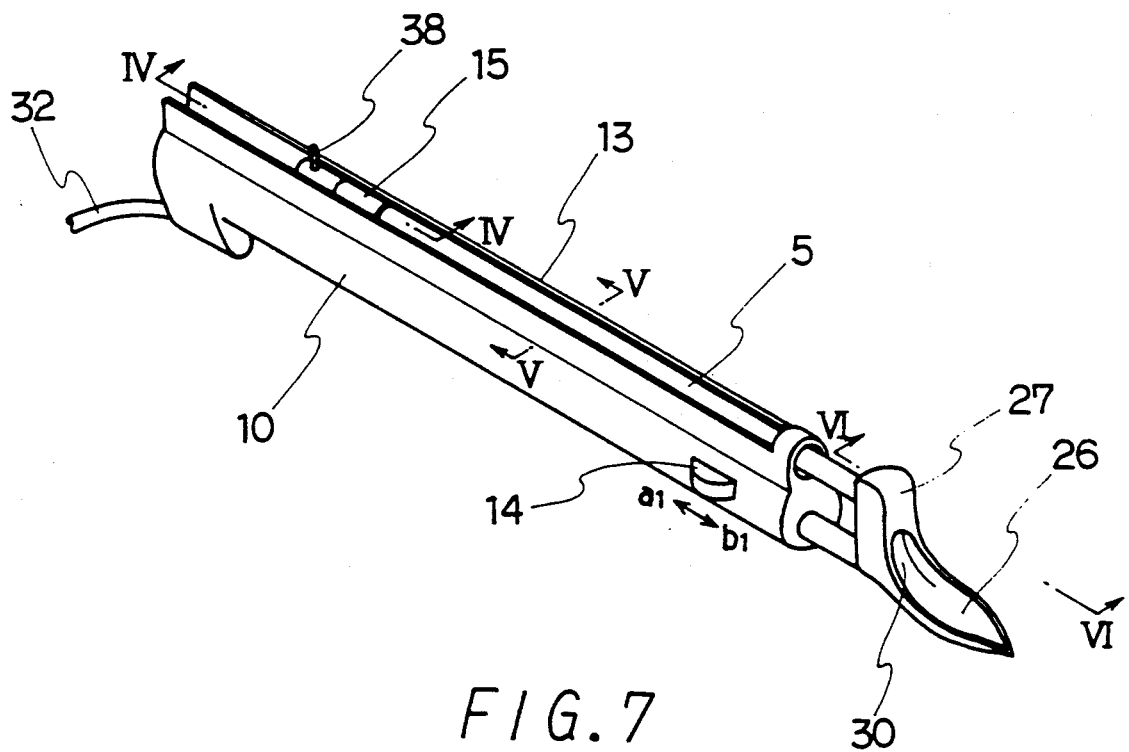
FIG. 6 is a perspective view showing the second embodiment of the tool of the present invention.

The numeral 28 shown in FIG. 5 is a heater attached in the rear end of the spatula 26 (the lower end of the wax melter 27), and a ceramic heater or the like can be used as the heater. By the heater 28, the wax melter 27 and the spatula 26 are heated to about 100° C. Moreover, the heating temperature by the heater 28 is selected from a range from about 80° to 120° C. according to the wax material.

The heater 28 is buried within a heater shaft 29 fixed in the handle portion 10. The above heater shaft 29 is inserted into a hole 30 formed in the rear end of the spatula 26. By employing the above-mentioned construction, various kind of spatulas 26 having different shapes can be utilized by exchanging them according to the use thereof. However, it is naturally possible to integratedly form the heater 28, the spatula 26 and the wax melter 27, and furthermore the construction thus integrated can be exchangeably attached to the handle portion 10.

The wax melter 27 has a wax delivery hole 31. The wax, which is abutted against the heated wax melter 27 and thereby melted, flows down through the delivery hole 31 in the direction of the arrow A and stays in the spatula 26 having a shape almost like a dish.

In FIG. 1, the numeral 32 shows an electric cord connected to the rear end of the handle portion 10, which passes through the handle portion 10 and brings electricity from the power source to the heater 28.

Next, there is explained the manner to use the tool having the above-mentioned construction.

To begin with, the first drive 15 is attached to one end (the rear end) of the wax cartridge 16. Namely, the clip 18 is opened, and the rear end of the wax cartridge 16 is clamped so as to be resiliently held. Thereafter, the first drive 15 and the wax cartridge 16 is accommodated in the wax cartridge holder 13 in such manner that the stem 25 of the connector 24 is inserted into the hole 19 in the first drive 15.

In the early state, the wax cartridge 16 is set with the front end thereof being slightly apart from the wax melter 27 (about 2 to 5 mm). Next, if it is required for the wax to be melted, the roller should be rotated in the direction of the arrow a1 with a fingertip. Thereby, the first pulley 20 also rotates in the direction of the arrow a1, and the string 23 circulates in the direction of the arrow a2. Therewith, the connector 24 moves forward, namely in the direction of the arrow a2, and thereby the wax cartridge 16 is moved forward through the base 17 and the clip 18.

The wax, which is abutted against the wax melter 27 and thereby melted, flows through the delivery hole 31 into the spatula 26 and temporarily stays therein. The melted wax, which stays in the spatula 26, is flowed into the region where a shaped wax is formed, and thereby the work of building and shaping an artificial denture model is carried out.

If it is required to melt a lot of wax rapidly, the roller 14 should be strongly rotated in the direction of the arrow a1. On the other hand, if it is required to melt a little wax, the roller 14 should be slightly rotated in the same direction.

If it is required to stop melting the wax, the roller 14 should be rotated in the reverse direction, namely in the direction of the arrow b1. Therewith, the first pulley 20 also rotates in the direction of the arrow b1 and the string 23 circulates in the direction of the arrow b2. Thereby, the connector 24 is moved backward in the direction of the arrow b2, and accompanied with the backward movement of the base 17 and the clip 18, the wax cartridge 16 is moved backward. Consequently, the tip of the wax cartridge 16 is separated from the wax melter 27 and thereby the wax melting is stopped.

The above-mentioned roller 14 is repeated to rotate forward (the arrow a1) and backward (the arrow b1), and thereby the work of building and shaping the model is carried out while melting a desired amount of wax.

If it is consumed, the wax cartridge 16 should be exchanged. In this case, the base 17 and the clip 18 are pulled out from the stem 25 of the connector 24 together with the wax cartridge 16. Moreover, the roller 14 is rotated in the direction of the arrow b1 to move the connector 24 backward. Subsequently, the new wax cartridge 16 is clamped in the clip 18 again, the wax cartridge 16 is mounted on the wax cartridge holder 13 as described above and at the same time, the stem of the connector 24 is inserted into the hole 19 in the base 17.

Next, there is explained the second embodiment of the wax shaping tool of the present invention referring to FIGS. 6 to 9.

The tool of the second embodiment has a construction similar to the one in the first embodiment except for the wax feed mechanism. Therefore, the same reference numeral represents the same parts and the explanation is omitted. Moreover, in the case of the present embodiment, the bore 11 and the slit 12 are held open on the rear end of the handle portion 10.

Figure 7:
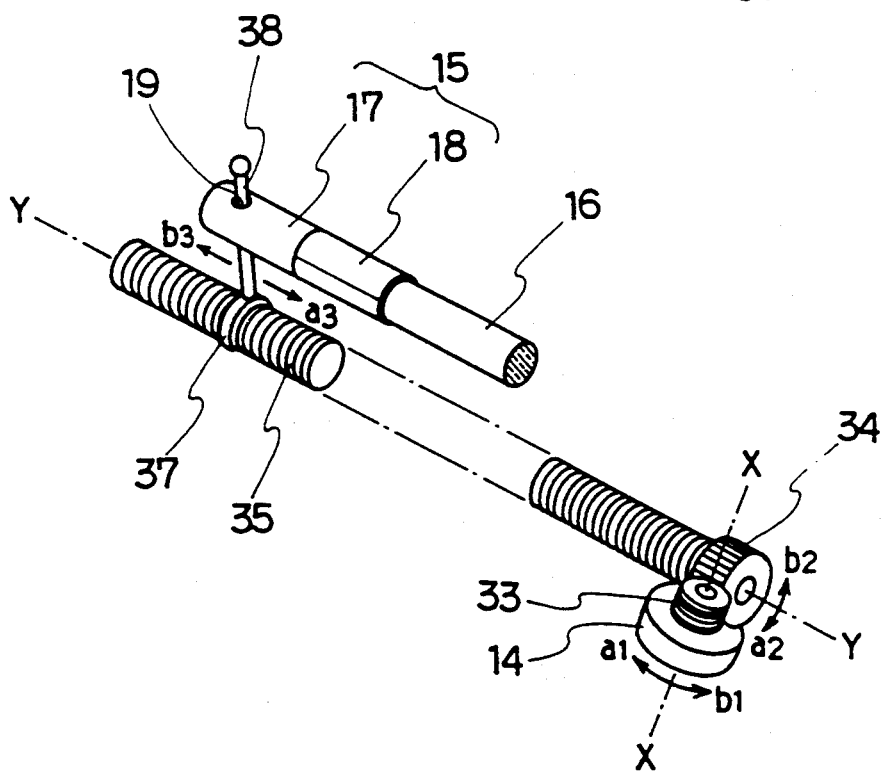
FIG. 7 is a perspective view showing a wax feeding mechanism in the tool in FIG. 6.
Figure 8:
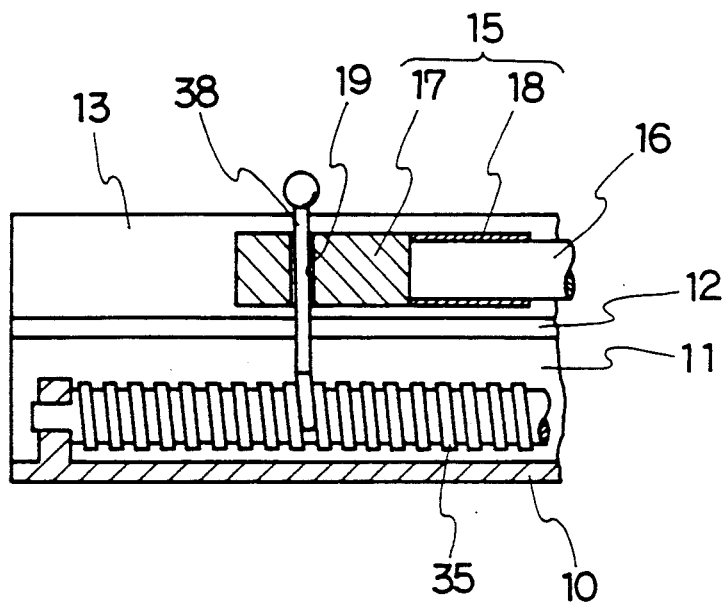
FIG. 8 is a sectional view taken along the line IV—IV in FIG. 6.
Figure 9:
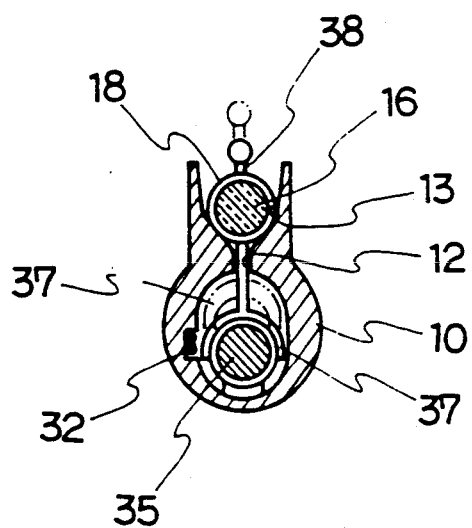
FIG. 9 is a sectional view taken along the line V—V in FIG. 6.

In FIG. 7, a first gear 33 to be rotated with the roller 14 is fixed on the center axis X of the roller 14 which is rotatably mounted on the handle portion 10.

Moreover, in the bore 11 of the handle portion 10, a worm or screw 35, which has rotational axis Y coaxial with the longitudinal axis of the handle portion (10), and of which tooth is cut in the slightly inclined direction perpendicular to the rotational axis Y, is rotatably provided. Furthermore, a second gear 34, which engages with the first gear, is rotatably supported to rotate with the screw 35.

By employing the above-mentioned construction, the screw 35 can be driven according to the rotation of the roller 14.

The above-mentioned conversion of the rotary driving force can be performed by means of a combination of the above-mentioned first gear 33 and the second gear 34 as well as a straight bevel gear, a spiral bevel gear, a face gear, a screw gear, or the like. Furthermore, a cylindrical gear can be used in place of the screw 35 so as to be directly driven by means of the first gear which engages therewith. Moreover, the axis of the roller 14 can be make parallel to the screw 35, and thereby the mutual combination of the parallel gears can be used.

A connector 36, which converts the rotating movement into the back-forth movement of the screw 35 and transmits it to the base 17, is provided on the screw 35. The connector 36 comprises an horseshoe clip 37 having a shape like a fork which engages with the screw 35 and a supporting shaft 38 which projects in the transverse direction to the cylindrical gear 35. The screw 35 and the horseshoe clip 37 constitute a conversion mechanism for converting the rotating movement into the rectilinear movement.

The horseshoe clip 37 is formed almost like a "U"-shape, which engages with the flight of the screw 35. The above-mentioned horseshoe clip 37 is formed with the material such as metal or plastic and has spring property. Therefore, when the upper end of the supporting shaft 38 is pressed down, the horseshoe clip 37 engages with the screw 35 with clock feeling.

On the contrary, when the supporting shaft 38 is pulled up, the horseshoe clip 37 is removed (the above-mentioned state is shown by the phantom line in FIG. 9), and the horseshoe clip 37 becomes free. Therefore, the first drive 15 can be freely moved forward or backward irrespective of the operation of the screw 35. The supporting shaft 38 penetrates through the slit 12 into the hole 19 in the base 17 in the position where the supporting shaft 38 reaches. The wax feed mechanism is comprised of the first gear 33, the second gear 34, the screw 35 and the connector 36 described above.

Next, there is explained a manner to use of the above-mentioned tool.

First, the rear end of the wax cartridge 16 is clamped by opening the clip 18 so as to be resiliently held similar to the first embodiment.

Thereafter, the supporting shaft 38 of the connector 36 is penetrated through the hole in the base 17, and the horseshoe clip is entered into the bore 11 with the upper end of the supporting shaft 38 pulled up. Then the position of the wax cartridge is adjusted and the stem is depressed down to engage the horseshoe clip 37 with the screw 35. At that time, the wax cartridge 16 is concurrently accommodated in the wax cartridge holder 13.

In the early state, the wax cartridge 16 is set with the front end thereof being slightly apart from the wax melter 27 (about 2 to 5 mm).

Secondly, if it is required to melt the wax, the roller 14 is rotated by a fingertip in the direction of the arrow a1. Thereby, the first gear 33 rotates in the direction of the arrow a1, and the second gear 34 and the screw 35 rotates in the direction of the arrow a2, respectively. Therewith, the horseshoe clip 37 of the connector 36 moves forward, namely in the direction of the arrows a3 and thereby the wax cartridge 16 is moved forward.

Then, the work of building and shaping an artificial denture model is performed while melting the wax cartridge 16 similar to the first embodiment.

When the wax cartridge 16 is consumed and therefore exchanged, the supporting shaft 38 of the connector 36 should be lifted and the horseshoe clip 37 should be removed from the cylindrical gear 35.

In that state, the connector 36 is moved backward to be pulled out from the rear end of the handle portion 10, a new wax cartridge 16 should be clamped in the clip 18 again and set along with the connector 36 as described above.

Being similar to FIGS. 1 to 5, in the tool of the present embodiment, the user can freely control the forth-back motion of the wax cartridge by rotating the roller and can freely adjust the amount and speed of wax melting speed by controlling the rotary direction and the rotary speed of the roller with fingers.

INDUSTRIAL AVAILABILITY

According to the tool of the present invention, the wax cartridge is moved forward by the pressure from the rear end thereof, and is abutted against the wax melter and thereby melted, with the wac cartridge mounted and accommodated in the wax cartridge holder. Therefore, the present tool is different from the conventional tool mainly because in the present tool any external force which deforms the wax cartridge is not applied. Accordingly, even if the wax cartridge is apt to be softened in the room temperature and deformed by a slight force, the rectilinear cylindrical shape is held and the wax melting can be rapidly performed.

Moreover, according to the tool of the present invention, the wax cartridge can be moved forward as the roller rotates in the forward direction, and the wax cartridge can be moved backward as the roller rotates in the backward direction. Furthermore, the speed of movement of the wax cartridge can be controlled by the rotary speed of the roller. Therefore, it is possible for the wax cartridge to be rapidly melted in a short time and to be slowly melted little by little. Thereby, it is very convenient for the wax cartridge to be adjusted to the various dental technical operations.

Moreover, if the heating and melting condition continues for hours, this kind of wax is usually caused to be degenerated or deteriorated. However, since the heating and melting of the wax is performed just before shaping thereof by means of the tool of the present invention, the degeneration or deterioration of the wax is not caused.

I claim:

1. A wax shaping tool comprising: a tubular handle portion having a slit extending in an axial direction for interconnecting an internal bore with the external space;
   a wax cartridge holder provided on upper side of the handle portion including edges of said slit for slidably guiding a wax cartridge;
   a roller rotatably provided onto said handle portion so as to protrude from a peripheral part thereof;
   a first drive which removably holds a rear end of said wax cartridge and is movable in an axial direction in the wax cartridge holder;
   a second drive provided in said handle portion for converting a rotating movement of said roller into the rectilinear movement and for transmitting the motion to said first drive;
   a spatula provided on a front end of said handle portion;
   a wax melter for contacting and melting the wax cartridge projected out of a front end of said wax cartridge holder; and
   a heater for heating up said spatula and said wax melter.

2. The tool of claim 1, wherein said second drive comprises:
   a first pulley which rotates with said roller;
   a second pulley rotatably provided in a rear end of said bore;
   a string strained between said first and second pulleys; and
   a connector portion having a lower portion fixed to said string and a stem removably connected through the slit to the first drive.

3. The tool of claim 1, wherein said second drive comprises:
   a screw member provided in said bore, along a longitudinal direction of the bore; said screw member being rotatable around a self-shaft;
   a gear means for transmitting the rotating movement in both rotational directions of said roller to a forth-back movement of said screw material; and
   a connector having an engaging portion which removably engages with said screw member and moves backward and forward according to rotating movement of said screw member, and a stem fixed on said engaging portion and removably connected through said slit to said first drive.

4. The tool of claim 1, wherein said second drive comprises:
   a stem inserted through the slit and having an upper end removably engaging with the first drive; and
   a conversion means for converting the rotation of the roller into the rectilinear movement and thereby rectilinearly driving the lower end of the stem; said conversion means being housed in the bore.

* * * * *